United States Patent [19]

Arndt et al.

[11] Patent Number: 4,526,705
[45] Date of Patent: Jul. 2, 1985

[54] LIGHT-COLLECTING SYSTEMS AND THE USE OF COUMARIN DERIVATIVES AS ENERGY CONVERTERS IN THEM

[75] Inventors: Frank Arndt, Krefeld; Uwe Claussen, Leverkusen; Horst Harnisch, Much; Carl-Wolfgang Schellhammer, Bergisch Gladbach, all of Fed. Rep. of Germany

[73] Assignee: Bayer Aktiengesellschaft, Leverkusen, Fed. Rep. of Germany

[21] Appl. No.: 451,587

[22] Filed: Dec. 20, 1982

Related U.S. Application Data

[63] Continuation of Ser. No. 223,882, Jan. 9, 1981, abandoned.

[30] Foreign Application Priority Data

Jan. 19, 1980 [DE] Fed. Rep. of Germany ....... 3001877

[51] Int. Cl.³ ................ C09K 11/02; C09K 11/06
[52] U.S. Cl. .............. 252/301.32; 250/361 R; 250/483.1; 252/301.16; 252/301.17; 252/301.34; 252/301.35; 548/159; 548/224
[58] Field of Search ............ 252/301.16, 301.17, 252/301.32, 301.34, 301.35; 548/159, 224; 250/361 R, 483.1

[56] References Cited

U.S. PATENT DOCUMENTS 3,521,187  7/1970  Snavely et al. ............ 252/301.17
4,035,740  7/1977  Schäfer et al. .

FOREIGN PATENT DOCUMENTS 1764982 10/1972 Fed. Rep. of Germany .
2411969  9/1975 Fed. Rep. of Germany .
2702237  7/1978 Fed. Rep. of Germany ............ 252/301.17
2837257  3/1979 Fed. Rep. of Germany .
1338020  8/1963 France .
 428953  7/1967 Switzerland .
1020815  2/1966 United Kingdom .
2017133 10/1979 United Kingdom .

Primary Examiner—Arthur P. Demers
Attorney, Agent, or Firm—Sprung Horn Kramer & Woods

[57] ABSTRACT

Light-collecting system, characterized in that it contains a coumarin derivative of the formula

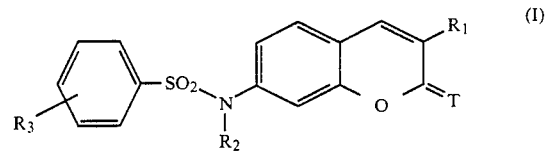

in which T designates O or $NR_4$, wherein $R_4$ represents hydrogen, optionally substituted alkyl or optionally substituted aryl;

$R_1$ designates a carbocyclic or heterocyclic, oxygen-free 5-membered or 6-membered ring which is linked via a C atom or a 5-membered or 6-membered heterocyclic ring which is linked via an N atom and which rotates unsymmetrically about an axis passing through the coumarin-N-heterocyclic ring linkage, it being possible for the 5-membered or 6-membered rings mentioned to carry non-ionic substituents and for an optionally substituted benzene ring or an optionally substituted naphthalene ring to be fused onto them;

$R_2$ designates hydrogen, alkyl, cycloalkyl, aralkyl or aryl, it being possible for the hydrocarbon radicals mentioned to be substituted, and $R_3$ designates hydrogen, alkyl, cycloalkyl, aralkyl, aryl or a $-OR_5$, $-SO_2R_5$, $-SO_2NHR_5$, $-NHCOR_5$, halogen or $COOR_5$ radical, wherein $R_5$ represents alkyl, cycloalkyl, aralkyl or aryl, and the use of coumarin derivatives as energy converters in light-collecting systems.

18 Claims, No Drawings

LIGHT-COLLECTING SYSTEMS AND THE USE OF COUMARIN DERIVATIVES AS ENERGY CONVERTERS IN THEM

This is a continuation of application Ser. No. 223,882, filed Jan. 9, 1981, now abandoned.

BACKGROUND OF THE INVENTION

Devices for collecting diffuse electromagnetic radiation by utilizing the fluorescence are known. The core of the collectors is a medium which has a greater optical density than its surroundings and which contains centers which are capable of fluorescence (German Offenlegungsschrift No. 2,620,115).

The economic applicability of a light-collecting system is to a large extent determined by the usefulness of the dyestuff employed therein as a light converter. Extreme demands are made on the optical quality of this dyestuff [Appl. Phys. 14 123–139 (1977)].

SUMMARY OF THE INVENTION

The invention relates to new light-collecting systems, which are characterized in that they contain, as energy converters, a coumarin derivative of the formula

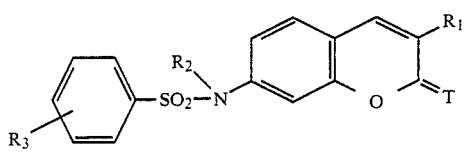

In formula (I): T denotes O or $NR_4$, wherein $R_4$ represents hydrogen, optionally substituted alkyl or optionally substituted aryl;

$R_1$ denotes a carbocyclic or heterocyclic, oxygen-free 5-membered or 6-membered ring which is linked via a C atom or a 5-membered or 6-membered heterocyclic ring which is linked via an N atom and which rotates unsymmetrically about an axis passing through the coumarin-N-heterocyclic ring linkage, it being possible for the 5-membered or 6-membered rings mentioned to carry non-ionic substituents and for an optionally substituted benzene ring or an optionally substituted naphthalene ring to be fused onto them;

$R_2$ denotes hydrogen, alkyl, cycloalkyl, aralkyl or aryl, it being possible for the hydrocarbon radicals mentioned to be substituted, and $R_3$ denotes hydrogen, alkyl, cycloalkyl, aralkyl, aryl or a $-OR_5$, $-SO_2R_5$, $-SO_2NHR_5$, $-NH-COR_5$;$CO-OR_5$ or halogen radical, wherein $R_5$ represents alkyl, cycloalkyl, aralkyl or aryl.

$R_1$ preferably represents a 5-membered or 6-membered heterocyclic ring which contains 1, 2 or 3 hetero-atoms N or S and onto which a benzene ring can be fused, it being possible for both the heterocyclic ring and the fused-on benzene ring to be substituted by, for example, alkyl, aryl, aralkyl, cycloalkyl, halogen, alkoxy, cyano or acyl.

Examples which may be mentioned of $R_1$ in the meaning of a 5-membered or 6-membered heterocyclic ring onto which a benzene ring can be fused are: pyrazole, imidazole, thiazole, 1,2,4-triazole, 1,3,4-thiadiazole, benzimidazole, benzthiazole, pyridine and benzpyrimidone.

$R_1$ particularly preferably represents a heterocyclic radical of the formula

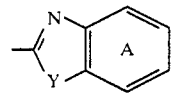

in which Y designates $NR_6$ or S, wherein $R_6$ represents alkyl, aryl, cycloalkyl or aralkyl, and the ring A can be substituted by alkyl, alkylsulphonyl, aryl, aralkyl, cycloalkyl, halogen, alkoxy, cyano or acyl.

Alkyl ($R_1$, $R_2$, $R_3$, $R_4$, $R_5$, $R_6$, A) preferably represents $C_1$–$C_6$-alkyl.

Aryl ($R_1$, $R_2$, $R_3$, $R_4$, $R_5$, $R_6$, A) preferably represents phenyl.

Cycloalkyl ($R_1$, $R_2$, $R_3$, $R_5$, $R_6$, A) preferably represents $C_3$–$C_7$-cycloalkyl, in particular cyclopentyl or cyclohexyl.

Aralkyl ($R_1$, $R_2$, $R_3$, $R_5$, $R_6$, A) preferably represents benzyl or phenethyl.

Acyl ($R_1$, A) preferably represents ($C_1$–$C_8$-alkyl)carbonyl, benzoyl, $C_1$–$C_6$-alkylsulphonyl or phenylsulphonyl.

Halogen ($R_1$, A) preferably represents chlorine, bromine or fluorine.

Alkoxy ($R_1$, A) preferably represents $C_1$–$C_6$-alkoxy. Substituted alkyl ($R_2$, $R_4$) which can be substituted, for example, by halogen, such as chlorine or bromine, cyano, trifluoromethyl, $C_1$–$C_6$-alkoxy, $C_1$–$C_6$-alkylsulphonyl, phenylsulphonyl, carbamoyl which is monosubstituted or disubstituted by $C_1$–$C_6$-alkyl or phenyl, carbamoyl, sulphamoyl, sulphamoyl which is monosubstituted or disubstituted by $C_1$–$C_6$-alkyl or phenyl, or amino which is monosubstituted or disubstituted by $C_1$–$C_6$-alkyl or phenyl.

Substituted aryl ($R_2$, $R_4$), substituted cycloalkyl ($R_2$) and substituted aralkyl ($R_2$) represent hydrocarbon radicals which, in addition to the substituents mentioned above for alkyl, can also be substituted, for example, by $C_1$–$C_6$-alkyl.

Further compounds which can preferably be used as light converters are coumarin derivatives of the formula

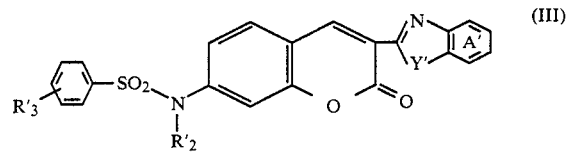

in which $R_2'$ designates hydrogen or $C_1$–$C_4$-alkyl, in particular methyl or ethyl, $R_3'$ designates hydrogen, $C_1$–$C_4$-alkyl, in particular methyl or ethyl, $C_1$–$C_4$-alkylsulphonyl, phenylsulphonyl, $C_1$–$C_4$-alkoxy or phenoxy and $Y'$ designates $NR_6'$ or S, wherein $R_6'$ designates $C_1$–$C_4$-alkyl, in particular methyl, or phenyl, and wherein the ring A' can be substituted by $C_1$–$C_4$-alkyl, in particular methyl, $C_1$–$C_4$-alkoxy, in particular methoxy, or halogen, in particular chlorine.

DETAILED DESCRIPTION OF THE INVENTION

The compounds of the formula (I) which can be used, according to the invention, as energy converters in light-collecting systems are known (see, for example, German Offenlegungsschrift (German Published Specification) No. 2,702,237), or they can be prepared by processes analogous to those known from the literature.

The new light-collecting systems, which are shaped articles with a suitable geometry, that is to say optical systems, in which the ratio of the emission surface to the absorption surface can be 1:50 to 1:2,000, are suitable for absorbing incident diffuse electromagnetic radiation and for emitting it, almost without loss, in a medium which has an optical density higher than that of its surroundings, whereby most of the emitted light remains totally reflected in the medium.

Only the portion of emitted light of which the emission band is largely free from absorption can be used for the purpose according to the invention.

It is thus expedient for the dyestuffs of the formula (I) to be especially purified before use in the light-collecting systems. In particular, they must be largely free from impurities which absorb long wavelengths.

The invention accordingly preferably relates to light-collecting systems which are characterised in that they contain a dyestuff of the formula (I) which, in a 0.05% strength solution, for example in chloroform, exhibit a rise in transmission of 0% to >90% at a change in wavelength of 25-100 nm, preferably 25-45 nm, measured with a cell thickness of 10 cm.

In favorable cases, the dyestuffs can be purified by repeated careful crystallization. Separation by column chromatography on solid supports, such as $Al_2O_3$ or $SiO_2$, is necessary in most cases. High degrees of purity are obtained in a particularly mild manner by partition chromatography, for example by steady-state (O'Keefe) partition or Craig countercurrent partition.

The new light-collecting systems can be used, for example, in connection with solar cells for utilizing solar energy and in scintillators of a known type [see, for example, J. B. Birks: The Theory and Practice of Scintillation Counting (Pergamon Press, London 1964); J. Opt. Am. 39, 912 (1949); J. Appl. Phys. 40, 3544 (1969); Nuclear Instruments and Methods 87, 111–123 (1970); Research Disclosure, page 43 (1977); and DE-OS (German Published Specification) No. 2,629,641]. Moreover, they are suitable in connection with electronic controls as display devices with a very low energy consumption, and they are also suitable, without electronic components, for various display, information and marking purposes, for example in passive display elements, information signs and traffic signs, such as traffic lights.

The light-collecting systems according to the invention contain the dyestuff dissolved in a liquid or a solid, the most diverse geometric shapes being possible, depending on the field of use of the light-collecting system. Suitable solid media such as are employed, for example, for collecting light in connection with solar cells and in passive display elements are, for example, plastics which transmit light and can be used for optical purposes, such as homopolymers and copolymers of acrylic acid (derivatives) or polycarbonates. Furthermore, the light-collecting systems can also contain the dyestuff dissolved in a liquid—for example an alcohol, ketone, halogenated hydrocarbon or ether. Solvents which are particularly suitable are, for example, ethanol, propanol, methyl ethyl ketone, acetone, cyclohexanone, chloroform, perchloroethylene and glycol monomethyl ether.

It is preferable to use the dyestuffs of the formula (I) in solids.

The use, according to the invention, of the dyestuffs of the formula (I) is highly advantageous since, in addition to a good quantum yield and a high amplification factor, they have excellent fastness to light and thus ensure that the new light-collecting systems can be used economically.

It must be described as surprising that the dyestuffs of the formula (I) are suitable for advantageous use in light-collecting systems, since numerous highly fluorescent dyestuffs, such as, for example, rhodamine G, cannot be used. The already very substantial requirements imposed on the optical quality of laser dyestuffs are likewise in many cases not sufficient to recommend the use of these dyestuffs in light-collecting systems.

EXAMPLES

EXAMPLE 1

4 g of 3-benzthiazolyl-7-phenylsulphonylaminocoumarin are dissolved in 60 ml of chloroform and the solution is chromatographed on 800 g of silica gel (Merck). The eluting agent is ethyl acetate/methanol 3:1. 3.2 g of a product are obtained and the product is recrystallized from n-butanol.

500 mg of the compound are dissolved in 1 liter of $CHCl_3$ and the transmission T is measured with a cell thickness of 10 cm. The transmission is 0% at 449 nm and 93% at 479 nm. The fluorescent quantum yield $\Phi$ is 0.87, the Stokes shift $\Delta$ is 88 nm and the proportion of useful fluorescence is 79%.

By the "proportion of useful fluorescence" there is understood the percentage proportion of the fluorescence light originally emitted which is not lost by reabsorption.

If the procedure followed is analogous to that in Example 1 using the compounds listed in the table below, the measurement results given are obtained.

TABLE

| Example | $R_1$ | $R_2$ | $R_3$ | $\Phi$ | $\Delta$ [nm] | Proportion of useful fluorescence [%] |
|---|---|---|---|---|---|---|
| 2 | (benzimidazolyl, N-CH₃) | H | H | 0.90 | 137 | 92 |
| 3 | (benzimidazolyl, N-phenyl) | H | H | 0.77 | 117 | 88 |
| 4 | (benzothiazolyl, with OCH₃) | H | H | 0.86 | 100 | 66 |

To produce solid light-collecting systems, the compounds of Examples 1-4 are incorporated, to the extent of 0.1% by weight, in commercially available polyacrylate or polymethacrylate, the coloured plastic is granulated and the granules are pressed to sheets of suitable geometry.

We claim:

1. In a light-collecting system comprising an emission surface and an absorption surface wherein the ratio of the emission surface to the absorption surface is 1:50–2,000, said light-collecting system comprising a medium which has a greater optical density than its surrounding and which has at least one center capable of fluorescence wherein said center contains an energy converter, the improvement wherein said energy converter comprises a coumarin derivative of the formula

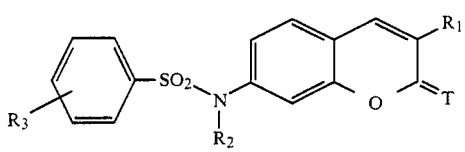

in which
T designates 0,
wherein
R$_1$ designates a pyrazolyl-, imidazolyl-, thiazolyl-, 1,2,4-triazolyl-, 1,3,4-thiadiazolyl-, benzimidazolyl-, benzthiazolyl-, pyridinyl-radical or a radical derived from benzpyrimidone, the heterocyclic radicals mentioned being unsubstituted or substituted;
R$_2$ designates hydrogen, and unsubstituted or substituted alkyl, cycloalkyl, aralkyl or aryl, and
R$_3$ designates hydrogen, alkyl, cycloalkyl, aralkyl, aryl or a —OR$_5$, —SO$_2$R$_5$, —SO$_2$NHR$_5$, —NH-COR$_5$, halogen or COOR$_5$ radical,
wherein
R$_5$ represents alkyl, cycloalkyl, aralkyl or aryl, and wherein said medium comprises a plastic which transmits light and can be used for optical purposes.

2. A light-collecting system according to claim 1, wherein the coumarin derivative is of the formula

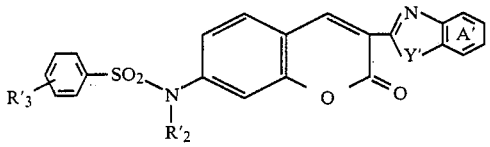

in which
R$_2'$ designates hydrogen or C$_1$–C$_4$-alkyl,
R$_3'$ designates hydrogen, C$_1$–C$_4$-alkyl, C$_1$–C$_4$-alkylsulphonyl, phenylsulphonyl, C$_1$–C$_4$-alkoxy or phenoxy and
Y' designates S,
and wherein the ring A' is unsubstituted or substituted by C$_1$–C$_4$-alkyl, C$_1$–C$_4$-alkoxy, or halogen.

3. A light-collecting system according to claim 1, wherein the coumarin derivative has been purified by repeated crystallization and/or column chromatography on solid supports and/or partition chromatography before use in the optical system.

4. A light-collecting system according to claim 1, wherein the coumarin derivative is in a 0.05% strength solution in chloroform, exhibits a rise in transmission of 0% to 90% at a change in wavelength of 25 to 45 nm, measured with a cell thickness of 10 cm.

5. An optical system according to claim 1, wherein the dyestuff used, in a 0.05% strength solution in chloroform, exhibits a rise in transmission of 0% to >90% at a change in wavelength of 25 to 45 nm, measured with a cell thickness of 10 cm.

6. A light-collecting system according to claim 1, wherein the plastic is a homopolymer or copolymer of acrylic acid or its derivatives or is a polycarbonate.

7. A light-collecting system according to claim 6, wherein the plastic is a polyacrylate.

8. A light-collecting system according to claim 6 wherein the plastic is a polymethyacrylate.

9. A light collecting system according to claim 4, wherein said change of wavelength is 25 to 45 nm.

10. A light collecting system according to claim 1, wherein the heterocyclic radical has an unsubstituted or substituted benzene ring fused thereon.

11. A light-collecting system according to claim 1, wherein the heterocyclic radical has an unsubstituted or substituted naphthalene ring fused thereon.

12. A light collecting system according to claim 1, wherein the heterocyclic radical carry one or more non-ionic substituents.

13. A light-collecting system according to claim 1, wherein the heterocyclic radical has an unsubstituted or substituted benzene ring fused thereon.

14. A light-collecting system according to claim 1, wherein said 5-membered or 6-membered ring carry one or more non-ionic substituents.

15. A light-collecting system according to claim 1, wherein
R$_1$ designates

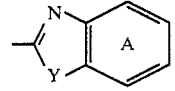

in which Y designates —NR$_6$ or S, wherein
R$_6$ represents alkyl, aryl, cycloalkyl or aralkyl and the ring A is unsubstituted or substituted by alkyl, alkylsulphonyl, aryl, aralkyl, cycloalkyl, halogen, alkoxy, cyano or acyl.

16. A light-collecting system according to claim 1, wherein
R$_1$ designates

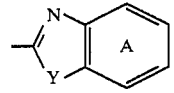

in which Y designates —NR$_6$ or S, wherein
R$_6$ represents alkyl, aryl, cycloalkyl or aralkyl and the ring A is unsubstituted or substituted by alkyl, alkylsulphonyl, aryl, aralkyl, cycloalkyl, halogen, alkoxy, cyano or acyl.

17. A light-collecting system according to claim 5, wherein the rise in transmission is 0% to 93%.

18. A light-collecting system according to claim 1, wherein said light-collecting system is in connection with an electronic control whereby the combination of said electronic control and said light-collecting system constitutes a display device.

* * * * *